United States Patent [19]
Colliot et al.

[11] Patent Number: 6,032,414
[45] Date of Patent: Mar. 7, 2000

[54] NURSERY BOXES FOR RICE SEED

[75] Inventors: François Colliot, Fontaines Saint-Martin, France; King-Su Fang, Taipei, Taiwan; Gilles Mussard, Saint Cyr au Mont d'Or, France; Michael Pilato, Raleigh, N.C.

[73] Assignee: Rhone-Poulenc Agrochimie, Lyons, France

[21] Appl. No.: 09/354,582

[22] Filed: Jul. 16, 1999

Related U.S. Application Data

[62] Division of application No. 08/966,801, Nov. 10, 1997, which is a division of application No. 08/786,788, Jan. 21, 1997, Pat. No. 5,716,977, which is a continuation of application No. 08/427,799, Apr. 26, 1995, abandoned, which is a continuation of application No. 08/138,192, Oct. 20, 1993, abandoned.

[30] Foreign Application Priority Data

Oct. 20, 1992 [FR] France .................................. 92 12816
May 18, 1993 [FR] France .................................. 93 06258

[51] Int. Cl.[7] .......................... A01N 43/40; A01N 43/56; A01G 9/02
[52] U.S. Cl. .......................... 47/65.5; 514/404; 514/407; 514/326
[58] Field of Search .................................. 514/407, 404, 514/326; 47/65.5

[56] References Cited

U.S. PATENT DOCUMENTS

| 4,804,675 | 2/1989 | Jensen-Korte et al. | 514/407 |
| 4,845,089 | 7/1989 | Lindig et al. | 514/210 |
| 4,945,165 | 7/1990 | Jensen-Korte et al. | 548/362 |
| 5,716,977 | 2/1998 | Colliot et al. | 514/407 |

FOREIGN PATENT DOCUMENTS

| 0201852 | 11/1986 | European Pat. Off. . |
| 0234119 | 9/1987 | European Pat. Off. . |
| 0245785 | 11/1987 | European Pat. Off. . |
| 0295117 | 12/1988 | European Pat. Off. . |
| 0303153 | 2/1989 | European Pat. Off. . |

OTHER PUBLICATIONS

*Chemical Abstracts*, vol. 118, No. 23, Jun. 7, 1993, abstract No. 228183c, abstract of Colliot et al, "FIPRONIL: A New Soil and Foliar Broad Spectrum Insecticide" in *Prot. Conf. Pest. Dis. 1992*, vol. 1, pp. 29–34 (Brighton Crop Protection Conference, Nov. 23–25, 1992).

*Primary Examiner*—Allen J. Robinson
*Attorney, Agent, or Firm*—Burns, Doane, Swecker & Mathis, L.L.P.

[57] ABSTRACT

A nursery box comprising a growth substrate for rice, rice seeds and an aqueous formulation for treating said rice seeds to protect rice plants against insects for a prolonged period of time.

24 Claims, No Drawings

NURSERY BOXES FOR RICE SEED

CROSS-REFERENCE TO RELATED APPLICATIONS

This application is a divisional of application Ser. No. 08/966,801, filed Nov. 10, 1997, now allowed, which is a divisional of application Ser. No. 08/786,788, filed Jan. 21, 1997, now U.S. Pat. No. 5,716,977, which is a continuation of application Ser. No. 08/427,799, filed Apr. 26, 1995, now abandoned, which is a continuation of application Ser. No. 08/138,192, filed Oct. 20, 1993, now abandoned.

The present invention relates to nursery boxes comprising a growth substrate for rice, rice seeds and an aqueous formulation for treating said rice seeds to protect rice plants against insects for a prolonged prior of time. The invention further relates to a new process for the treatment of rice crops using an insecticidal product other than an organophosphorus insecticide, and more especially a new process for the treatment of rice crops against parasites called stem borers (in Latin Chilo spp.) and plant hoppers (in Latin *Nilparvata lugens*), as well as other parasites such as weevils (in Latin *Lissorhoptrus oryzophilus*). Other parasites are advantageously eliminated by the process according to the invention, especially the nematode *Aphelencoides besseyi* and the mining fly *Hydrellia philiippina*.

Rice crops are attacked by a number of diseases, especially attacks from insects such as those mentioned above. In the case of paddy rice, there is a very particular difficulty in eliminating these insects since the possible treatment products tend to pollute the water in the paddy fields. Research is thus aimed at both treating rice plants effectively and vigorously against parasites and, at the same time, reducing water pollution to the bare minimum. The difficulty in solving this problem is particularly great because the two demands conflict with each other: if the number of treatments is reduced in order to reduce pollution, the quality of the protection is reduced. If the number of treatments is increased in order to increase the quality of the protection, pollution is also increased. There is thus no obvious solution to the problem to be solved, since the only possible solutions conflict with each other.

The problem of avoiding water pollution, in the case of rice cultivation, is all the more difficult since water for rice cultivation comprises various species, including useful insects or aquatic fauna, which are beneficial and profitable. It is necessary to destroy the harmful species without harming these profitable species.

Although insecticides available on the market and in the literature are very numerous, it so happens that there is virtually no satisfactory solution to the abovementioned problem.

A new process has now been found for growing rice seedlings according to the irrigated rice method which makes it possible to solve all or part of the abovementioned problems.

According to a first aspect of the invention, the latter relates to a process for treating rice plants or rice propagation material against insects with a view to obtaining a sustained and effective protection of the plant after the sowing period, characterised in that there is applied to the said plants or, preferably, to their propagation material, an effective amount of an insecticide other than an organophosphorus insecticide having systemic properties which is capable of having a long-lasting effect, that is to say even persisting on the growing plant after germination. More preferentially still, the propagation material used is the rice seed or, in other words, rice grains. Advantageously, the insecticidal material used is that which will be defined below.

According to another aspect of the invention, the latter relates to a process for the treatment of rice plants or of rice propagation material against insects, characterised in that no other treatment of the rice against insects is carried out for a period of 1 month, preferably for a period of 2 months, after sowing.

According to another aspect of the invention, the latter relates to a process for preventive, and optionally curative, treatment of rice propagation products and of the rice seedlings resulting therefrom against insect attacks, the said process consisting in applying to the (on and in the) rice propagation product an insecticidal active material having systemic properties which is capable of having a long-lasting effect. The insecticidal material used is preferably that which will be defined below.

According to another aspect of the invention, the latter relates to a process for preventive, and optionally curative, treatment of rice propagation products and of the rice seedlings resulting therefrom against insect attacks, the said process consisting in applying to the (on and in the) rice propagation product an insecticidal composition containing, as active material, an insecticide as already defined, as well as an agriculturally-acceptable vehicle and optionally an agriculturally-acceptable surface-active agent.

According to another aspect, the invention relates to a process for rice cultivation in which a rice seed is sown containing, inside the seed grains, an effective amount of an insecticide having systemic properties which is capable of having a long-lasting effect (that is to say even persisting on the growing plant after germination). According to this aspect of the invention, the rice can be sown directly in the paddy field but it can also be sown in nursery boxes. These nursery boxes are small boxes. They are used for the controlled germination of seeds or propagation material as well as for growing the young rice seedlings thus obtained during a very precocious stage of growth, before transplanting.

According to another aspect, the invention relates to a process for protecting rice grains, or rice seeds, for a long period against insects which cause damage to crops, and making them capable of conferring a long-lasting protection on the plants to which they will give birth, the said process being characterised in that rice grains are immersed or bathed or soaked in or impregnated with an aqueous formulation containing an insecticide as already defined.

In its various aspects mentioned above, the effective amount of active material required for protection according to the invention is generally between about 3 and 200 g/q (gram of active material per quintal of rice propagation material, preferably per quintal of seed, the weight of the latter being taken before soaking and/or impregnation), preferably between about 3 and 100 g/q, and more advantageously between about 6 and 25 g/q, these values representing the amount of active material effectively attached to the seed, in it or to its surface.

The invention further relates to rice seeds impregnated with such an insecticide having systemic properties which is capable of having a long-lasting effect.

The invention further relates to rice seeds wetted and impregnated with and/or soaked in an aqueous formulation comprising an insecticide having systemic properties which is capable of having a long-lasting effect, that is to say even persisting an the growing plant after germination.

This aqueous formulation intended for impregnating rice seeds can be fairly diverse in nature and is defined in practice so as to be able to ensure the incorporation in the said rice seed of the required effective amount of active material, as defined above. The formulation used in the invention can be of very varied type, for example a solution or a suspension or an emulsion or a suspoemulsion, or something else. The formulation used in the invention thus comprises, as necessary constituents, the active material and water; it optionally and additionally contains other customary constituents used in agrochemical formulations, for example those described in European Patent Application 295,117. However, among the compositions described in this European Patent Application, it is preferable to choose those which are more suited to rice seed impregnation. For example, the use of penetration agents can be particularly suitable for promoting penetration of the insecticidal active material into the said rice seed. The aqueous formulation used in the invention can also comprise another non-aqueous liquid phase.

According to a first embodiment of the invention commonly practised, the aqueous formulation used in the invention is obtained by diluting a concentrated formulation with water, this formulation being of any type known per se, for example a solution, a suspension, an emulsifiable concentrate, an emulsion, a suspoemulsion, a gel, a viscous liquid, a wettable powder, a dispersible granule, or something else. The diluted formulations used in the invention often have an active material content determined by the values shown hereinafter for the amount of active material absorbed by the seed and by the amount of aqueous formulation also absorbed or absorbable by the seed. This concentration, or dilution, can further vary within a very wide range according to the speed of impregnation which is desired, and according to the amount of effluent (that is to say, of formulation not absorbed by the seed) which is allowed (it will be seen below that a zero amount of effluent is preferred).

According to a specific variant of the invention, the aqueous formulation which has just been defined additionally comprises a significant amount of soil or compost or substrate/vehicle on and in which the rice seeds can germinate and the seedings can grow. This aspect of the invention makes it possible to produce nursery boxes for the germination of rice grains and their growth. The formulation considered according to the invention as an aqueous formulation is then the soil or vehicle for growth comprising a very high water content, itself comprising the insecticidal active material. This soil is not simply soil treated with an insecticide such as can be easily produced according to standard soil treatments, especially those described in European Application 295,117, but is then, quite obviously, soil, or a vehicle, containing sufficient water and insecticide for the rice seed, in contact with the soil, to be impregnated with a high amount of insecticidal active material, as defined above, to the point that the insecticidal protection affects not only the soil or vehicle but also the rice plant resulting from the germination and from the growth of the rice seed.

The invention thus further applies to nursery boxes containing
  a growth substrate. This substrate consists generally of natural or reconstituted soil or compost. It generally comprises clay and sand and binders and fertilisers,
  rice seed,
  an amount of water and insecticidal active material sufficient to produce seeds having the effective contents shown above of the said insecticidal active material. The latter ingredient (water+active material) is, according to another way of expressing it, an aqueous formulation as described hereinabove or hereinafter.

The size of the boxes is generally chosen to correspond to 100 to 300 boxes per hectare of cultivation, preferably 200 boxes. These boxes contain the amount of seed corresponding to a sowing of 10 to 300 kg/ha, preferably 20 to 200 kg/ha.

Although aqueous formulations of any type can be used in the invention, as well as systemic insecticidal active materials of the most varied natures, it is preferred to use, in the invention, active materials (and formulations containing them) which have little solubility in water, for example having a solubility in water of less than 100 ppm (=parts per million), preferably less than 50 ppm and more preferentially still less than 10 ppm. The solubilities which have just been referred to are intrinsic solubilities of the active material at a temperature of between 20° C. and 30° C., without taking into account solubilisations which can take place under the effect of the most varied solubilising agents or surface-active agents. The advantage of treatments according to the invention using such insecticidal active materials of low solubility is that the effectiveness of treatment is more consistent (especially in that the active material is not carried, after sowing, far from the seed or seeding by water, either by rain water or irrigation water) and longer lasting (mainly for the same reason, namely that the insecticidal active material has a better persistence of action in and close to the seed from which it is not far dispersed). It is understood that this relative insolubility of the insecticidal active material moreover has various consequences: the treatment according to the invention to produce seed impregnated with insecticidal active material can be relatively long (for example more than one day, indeed two days or more, the treatment generally lasting from about 10 minutes to 1 day or more, depending upon the particular active ingredient's affinity for the seed); another consequence is that the specific nature of the aqueous formulation used for treating the rice seed can vary within the widest limits (in nature and in content), as long as an adequate amount of active material remains close to the seed to be treated.

Although the insecticidal active material thus has little solubility in water, the formulation for seed treatment according to the invention still comprises a certain, very low, amount of active material in solution. As this is being absorbed by the rice grains, the non-solubilised part of the insecticide redissolves; in other words, by means of reciprocal equilibria, the insecticide not initially in solution can be transferred into the aqueous phase and into the rice grains. In this way, which corresponds to a progressive release, rice grains containing insecticide can be obtained both from a solution and from a suspension or other formulation containing insoluble insecticide.

The aqueous formulation which has just been discussed thus preferably consists of an aqueous liquid containing at least one liquid phase, itself consisting of a saturated solution of the systemic insecticide, and which can also contain other ingredients such as penetration agents, that is to say promoting penetration of the rice grains by the insecticide having systemic properties.

The invention thus further relates to a mass, or collection, of rice grains juxtaposed and soaked in and/or impregnated with and/or bathed in and/or immersed in an aqueous insecticidal formulation as defined above. In yet other words, the invention further relates to a collection of rice grains (especially in the form of nursery boxes or bags)

immersed in or soaked in or impregnated with or bathed in an aqueous insecticidal formulation as defined above. If the amount of aqueous liquid, and its concentration, with respect to the amount of seed grains to be treated and to the duration of absorption are suitably adapted, it is possible to immerse the grains in an aqueous formulation until these grains absorb from about 90 to 100% of the aqueous formulation, preferably from about 95 to 100%. This variant of the process of the invention is particularly advantageous in that it makes it possible to have no residual formulation which has to be discarded. In effect, if part of the formulation has been in contact with the seeds but has not been absorbed by the latter, then it cannot be reused and thus must be discarded. This variant of the invention thus greatly contributes to controlling pollution.

The invention also relates to the same masses of rice grains, or bags, in which the rice seed is in the form of grains which have already germinated, or, in other words, the invention relates to such masses, or bags, in which the rice grains already have their first radicle, and are at the same time immersed in or soaked in or impregnated with or bathed in an aqueous formulation as defined above and containing an insecticide of formula (I).

The invention further relates to a process for protecting rice grains, or rice seeds, for a long period of time against insects which cause damage to crops, and making them capable of conferring a long-lasting protection on the plants to which they give birth, the said process being characterised in that rice grains are immersed in or soaked in or impregnated with or bathed in an aqueous formulation as defined above and containing an insecticide of formula (I).

In the various processes for treating rice propagation products, preferably rice seeds, as defined immediately above and previously, the amount of aqueous formulation brought directly into contact with the seed (or rice propagation material) to be treated is generally between 15% and 300% of the weight of seed to be treated, preferably between 20 and 200%. Values outside these ranges, whether more or less, can also be used but without substantial or specific advantage. According to a specific embodiment, the amount of formulation used is equal to the maximum amount of aqueous formulation which the rice mass can absorb. This maximum amount can vary depending on various factors, especially depending on the temperature and the nature or variety of the specific rice seed treated. This amount is often between approximately 25 and 100% of the weight of the said rice seed.

According to yet another aspect, the invention relates to a process for propagating rice plants (or their seeds or rice propagation material) which consists in using a rice propagation material (or natural or artificial seed) soaked or impregnated beforehand with an aqueous liquid containing an insecticide having systemic properties and capable of having a long-lasting effect.

Advantageously, the various aspects of the invention, as they have been presented or as they will be presented [that is to say, the rice propagation material, the treated rice grains, the treated and germinated rice grains, the immersed masses, or bags of rice, the seed treatment processes, the curative or preventive treatment processes, the process for growing rice and the process for propagating rice plants and the insecticidal formulations suited to the aims according to the invention], are carried out with an effective amount of an insecticide having suitable systemic properties which is a pyrazole of formula 1-[phenyl(X)$_p$]-3-cyano-4-[R$^4$—S(O)$_n$]-5-R$^5$-pyrazole    (I), in which:

X represents a halogen atom or, in position 4 on the phenyl ring, an alkyl or alkoxy radical containing 1 to 4 carbon atoms and optionally substituted by 1 or a number of halogen atoms, especially fluorine, chlorine or bromine (which is represented hereinafter by the abbreviation haloalkyl and haloalkoxy), R$^4$ represents an alkyl or alkenyl or alkynyl radical containing 1 to 4 carbon atoms, optionally substituted by 1 or a number of halogen atoms, especially fluorine, chlorine or bromine, R$^5$ represents
- a hydrogen atom or
- a halogen atom or an alkyl or haloalkyl group having from 1 to 4 carbon atoms, or
- a linear or branched alkoxymethyleneamino group having from 2 to 5 carbon atoms and in which the methylene group can be unsubstituted or substituted by an alkyl group having from 1 to 4 carbon atoms, or
- a group R$^8$—S(O)$_n$ in which R$^8$ has either one or the other of the meanings given for R$^4$,
- an amino group
- an amino group —NR$^6$R$^7$ in which R$^6$ and R$^7$, which are identical or different, represent
    - a hydrogen atom or,
    - an alkyl, alkenylalkyl or alkynylalkyl or alkanoyl or haloalkanoyl or alkoxycarbonyl or haloalkoxycarbonyl group containing up to 5 carbon atoms, or
    - a formyl group, or
    - R$^6$ and R$^7$ together form, with the nitrogen atom to which they are attached, a 5- or 6-membered cyclic imide, n represents an integer equal to 0, 1 or 2, p represents an integer equal to 1, 2, 3, 4 or 5, preferably 1, 2 or 3 and more preferentially 3.

Preferentially, the substituents have the following meanings:

X represents a halogen atom in position 2 or 6 of the phenyl ring and a haloalkyl or haloalkoxy radical in position 4 on the phenyl ring, R$^4$ represents an alkyl or haloalkyl radical, R$^5$ represents a hydrogen or halogen atom or an amino group.

More preferentially still, the product of formula (I) is

1-[2,6-dichloro-4-CF$_3$phenyl]-3-cyano-4-CF$_3$S(O)$_n$-5-NH$_2$pyrazole.

The invention thus also relates to rice grains, in other words the rice seed, comprising the active material of formula (I) in the soaked state or impregnating the said seed (and not only coating the seed), preferably in the state saturating the said seed.

According to a variant of the invention, the rice grains are dry grains impregnated with the active material. According to another variant of the invention, the grains are damp grains, even wet grains, soaked in or, preferably, saturated with a solution or suspension containing the active material of formula (I).

The invention further relates to a process for growing rice in which the rice seed treated with a composition comprising an effective dose of product of formula (I) is sown, the said process comprising no other treatment (either of the seed or of the plant resulting therefrom) against insects (that is to say no other insecticidal treatment) for a period of 1 month after germination, preferably for a period of 2 months after germination, it being understood that the effectiveness of the process of the invention is even often sufficient not to require another insecticidal treatment beyond two months after sowing.

The principle of carrying out the seed treatment with insecticides as mentioned above was known per se, but only for the purpose of treating the seed, and not as a means of obtaining sustained and effective protection of the plant after the sowing period.

The invention thus also relates to a process for preventive, and optionally curative, treatment of rice propagation products and of the rice seedlings resulting therefrom against insect attacks, the said process consisting in applying to the (on and in the) rice propagation product, preferably the seed, an insecticidal composition containing the active material 1-[2,6-dichloro-4-CF$_3$phenyl]-3-cyano-4-CF$_3$SO-5-NH$_2$pyrazole, as well as an agriculturally-acceptable vehicle and optionally an agriculturally-acceptable surface-active agent.

According to yet another aspect, the invention relates to a process for the propagation of rice plants (or their seeds or rice propagation material) which consists in using a rice propagation material (or seed) treated beforehand using the active material 1-[2,6-dichloro-4-CF$_3$phenyl]-3-cyano-4-CF$_3$SO-5-NH$_2$pyrazole. This active material is in practice an effective amount to produce the expected result. The treatment using the said active material consists in applying to or in the rice propagation product an insecticidal composition containing the active material 1-[2,6-dichloro-4-CF$_3$phenyl]-3-cyano-4-CF$_3$SO-5-NH$_2$pyrazole, as well as an agriculturally-acceptable vehicle and optionally an agriculturally-acceptable surface-active agent.

The following examples, given as non-limiting examples, illustrate the invention and show how it can be used.

EXAMPLES 1 and 2

Rice seeds are treated using an aqueous formulation obtained by diluting, with water, a concentrated composition comprising 500 g/l of 1-[2,6-dichloro-4-CF$_3$phenyl]-3-cyano-4-CF$_3$SO-5-NH$_2$pyrazole. The two examples differ one from the other simply in the degree and the nature of the parasitic infestation.

The seeds are steeped, that is to say immersed for 24 h, in 100 l of aqueous insecticidal composition until the composition has been completely absorbed by the seed, in it and at its surface. The amount of water added to dilute the concentrated formulation is inferred from the active material content absorbed by the seed shown in the table below.

The seed is allowed to germinate and is then allowed to grow under normal conditions until harvesting. Measurements are carried out at various stages of development, these measurements relating either to the plants or to the parasites. A clump generally comprises between 20 and 50 rice stems.

The following results were observed:

The abbreviation DAS means "days after sowing".

Results of Example 1

| Content of active material in the seed in g/q | 3.1 | 6.2 | 12.5 | 25 | Untreated control |
|---|---|---|---|---|---|
| Percentage of germination | 96 | 98 | 96 | 98 | 92 |
| Number of adult weevils per transplanted rice clump; 7 DAS | 3.2 | 2.2 | 1.6 | 1.8 | 12 |

-continued

| Number of larval weevils per transplanted rice clump; 30 DAS | 6.2 | 3 | 1.8 | 1.6 | 26 |
|---|---|---|---|---|---|
| Percentage of plants damaged by weevils; 45 DAS | 12.1 | 5.2 | 3 | 2.6 | 40 |
| Number of plant hoppers per transplanted rice clump; 45 DAS | 9.8 | 8.2 | 6 | 4 | 28 |
| Number of plant hoppers per transplanted rice clump; 70 DAS | 28 | 16 | 12 | 8 | 72 |
| Percentage of leaves attacked by nematodes; 60 DAS | 26 | 14 | 8 | 3 | 49 |
| Height of rice plants in cm; 30 DAS | 61.2 | 64.6 | 65.6 | 66 | 56 |
| Yields in tonne/ha | 4.1 | 5.6 | 5.8 | 5.8 | 2.2 |

The infesting nematodes were of *Aphelencoïdes besseyi* type.

Results of Example 2

| Content of active material in the seed in g/q | 12.5 | 25 | 50 | 100 | Untreated control |
|---|---|---|---|---|---|
| Percentage of germination | 98 | 99 | 98 | 96 | 95 |
| Height of the rice plants in cm; 17 DAS | 16.4 | 17 | 17.2 | 16.8 | 13.4 |
| Number of tillers per plant; 30 DAS | 16.2 | 16.8 | 17.2 | 17 | 12 |
| Percentages of dead cores (damage of stem borers); 30 DAS | 1.2 | 0.8 | 0.6 | 0.4 | 8 |
| Percentages of dead cores (damage from stem borers); 50 DAS | 8 | 3.2 | 2.6 | 2.2 | 23 |
| Number of plant hoppers per transplanted rice clump; 30 DAS | 7 | 6 | 3.8 | 2.2 | 22.5 |
| Number of plant hoppers per transplanted rice clump; 60 DAS | 17 | 8.8 | 4.5 | 3.2 | 36 |
| Percentage of tillers attacked by the mining fly, 40 DAS | 1.2 | 0.6 | 0.2 | 0.3 | 22 |
| Yields in tonne/ha | 4.8 | 5.1 | 5.2 | 4.9 | 2.8 |

The mining fly is *Hydrellia Philippina*.

The tables above show the altogether remarkable results of the application according to the invention.

What is claimed is:

1. A nursery box which comprises:
   (i) a growth substrate for rice;
   (ii) rice seeds; and
   (iii) an aqueous formulation for treating said rice seeds to protect rice plants against insects for a prolonged period of time, said aqueous formulation comprising water and a compound having the formula $$1\text{-}(2,6\text{-dichloro-4-CF}_3\text{-phenyl})\text{-}3\text{-cyano-4-CF}_3\text{S(O)}_n\text{-}5\text{-NH}_2\text{-pyrazole} \qquad (I)$$

wherein n is 0, 1 or 2, in an amount sufficient to impregnate said rice seeds and effectively protect rice plants germinated from the impregnated seeds from insects for a period of at least two months after sowing, in the absence of any other insecticidal treatment of the impregnated seeds or of the rice plants germinated from the impregnated seeds.

2. A nursery box according to claim 1, wherein the amount of the aqueous formulation is between about 15 and 300% by weight of the rice seeds.

3. A nursery box according to claim 2, wherein the amount of the aqueous formulation is between about 20 and 200% by weight of the rice seeds.

4. A nursery box according to claim 1, wherein the amount of the compound of formula (I) impregnated into the rice seeds is between about 3 and 200 g/q.

5. A nursery box according to claim 4, wherein the amount of the compound of formula (I) impregnated into the rice seeds is between about 3 and 100 g/q.

6. A nursery box according to claim 5, wherein the amount of the compound of formula (I) impregnated into the rice seeds is between about 6 and 25 g/q.

7. A nursery box according to claim 1, wherein the rice seeds absorb from about 90 to 100% of the aqueous formulation.

8. A nursery box according to claim 7, wherein the rice seeds absorb from about 95 to 100% of the aqueous formulation.

9. A nursery box according to claim 1, having a size corresponding to from 1/100 to 1/300 of a hectare of cultivation.

10. A nursery box according to claim 9, having a size corresponding to 1/200 of a hectare of cultivation.

11. A nursery box according to claim 1, comprising an amount of rice seeds sufficient for sowing from 10 to 300 kg/ha.

12. A nursery box according to claim 11, wherein the amount of rice seeds is sufficient for sowing from 20 to 200 kg/ha.

13. A nursery box which comprises:
(i) a growth substrate for rice;
(ii) rice seeds; and
(iii) an aqueous formulation for treating said rice seeds to protect rice plants against insects for a prolonged period of time, said aqueous formulation comprising water and the compound 5-amino-3-cyano-1-(2,6-dichloro-4-trifluoromethylphenyl)-4-trifluoromethylsulphinylpyrazole, in an amount sufficient to impregnate said rice seeds and effectively protect rice plants germinated from the impregnated seeds from insects for a period of at least two months after sowing, in the absence of any other insecticidal treatment of the impregnated seeds or of the rice plants germinated from the impregnated seeds.

14. A nursery box according to claim 13, wherein the amount of the aqueous formulation is between about 15 and 300% by weight of the rice seeds.

15. A nursery box according to claim 14, wherein the amount of the aqueous formulation is between about 20 and 200% by weight of the rice seeds.

16. A nursery box according to claim 13, wherein the amount of said compound impregnated into the rice seeds is between about 3 and 200 g/q.

17. A nursery box according to claim 16, wherein the amount of said compound impregnated into the rice seeds is between about 3 and 100 g/q.

18. A nursery box according to claim 17, wherein the amount of said compound impregnated into the rice seeds is between about 6 and 25 g/q.

19. A nursery box according to claim 13, wherein the rice seeds absorb from about 90 to 100% of the aqueous formulation.

20. A nursery box according to claim 19, wherein the rice seeds absorb from about 95 to 100% of the aqueous formulation.

21. A nursery box according to claim 13, having a size corresponding to from 1/100 to 1/300 of a hectare of cultivation.

22. A nursery box according to claim 21, having a size corresponding to 1/200 of a hectare of cultivation.

23. A nursery box according to claim 13, comprising an amount of rice seeds sufficient for sowing from 10 to 300 kg/ha.

24. A nursery box according to claim 23, comprising an amount of rice seeds sufficient for sowing from 20 to 200 kg/ha.

* * * * *